United States Patent [19]

Cole

[11] Patent Number: 4,944,731
[45] Date of Patent: Jul. 31, 1990

[54] NEEDLE PROTECTION

[76] Inventor: John Cole, 33 Horsham Road, Pease Pottage, Near Crawley, Sussex, England, RH11 9AW

[21] Appl. No.: 324,255

[22] Filed: Mar. 14, 1989

[30] Foreign Application Priority Data

May 3, 1988 [GB] United Kingdom ............... 8810366
May 25, 1988 [GB] United Kingdom ............... 8812439
Jul. 14, 1988 [GB] United Kingdom ............... 8816783

[51] Int. Cl.⁵ ............................................ A61M 5/32
[52] U.S. Cl. ................................. 604/192; 604/263
[58] Field of Search ...................... 604/187, 192, 263

[56] References Cited

U.S. PATENT DOCUMENTS

| 4,664,259 | 5/1987 | Landis ........................... 604/263 X |
| 4,820,277 | 4/1989 | Norelli .......................... 604/263 X |
| 4,826,490 | 5/1989 | Byrne et al. ....................... 604/198 |

Primary Examiner—John D. Yasko
Attorney, Agent, or Firm—Kinney & Lange

[57] ABSTRACT

The invention provides a needle protector for a device incorporating a needle comprising at least one arm mounted or mountable at or generally adjacent to a hub, or blunt end of the needle, and hinged or articulated so as to be capable of folding along the needle such as to shield and protect the tip thereof, and being positively securable in that folded disposition.

2 Claims, 2 Drawing Sheets

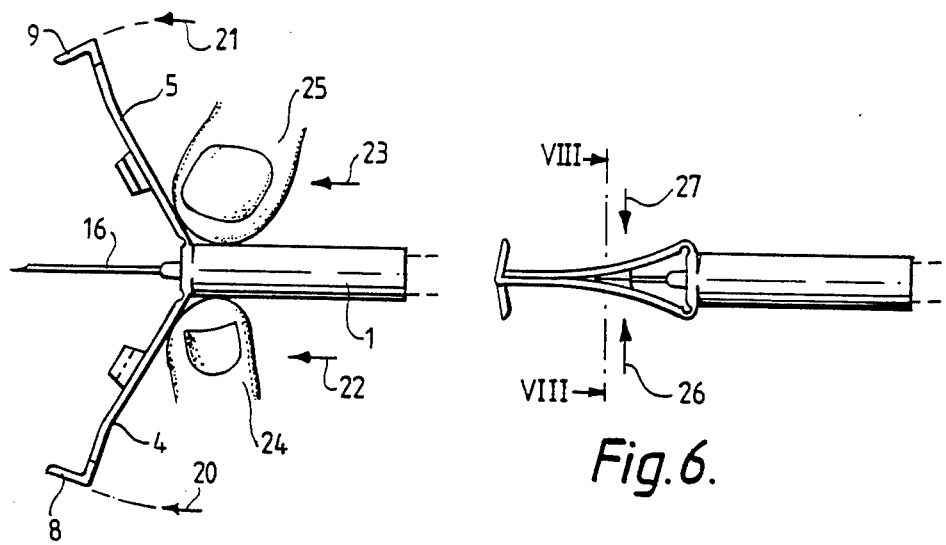
Fig.5.
Fig.6.
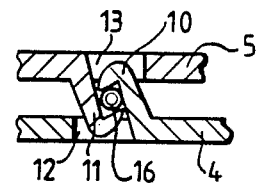
Fig.7.
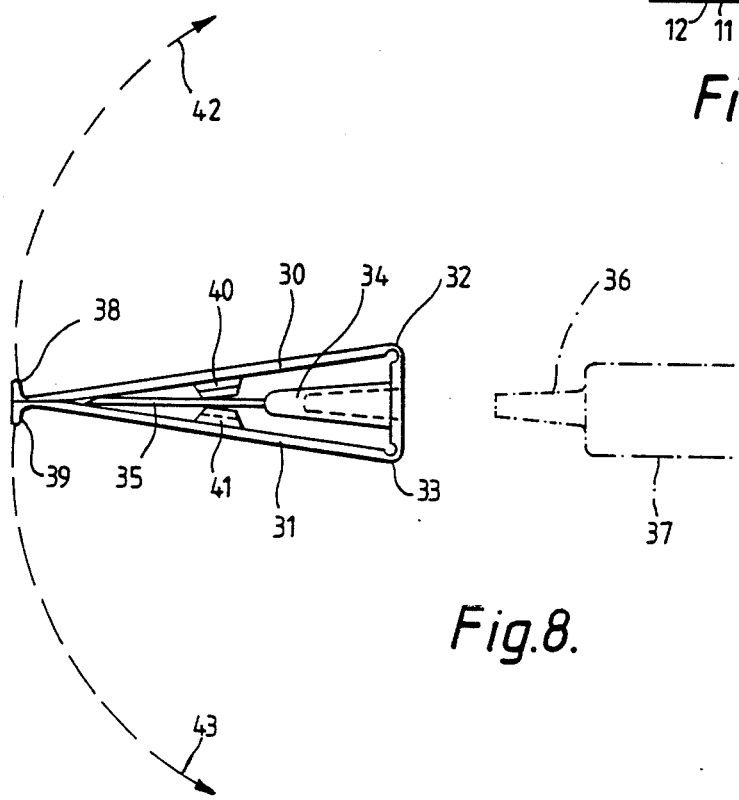
Fig.8.

NEEDLE PROTECTION

BACKGROUND OF THE INVENTION

1. Field of the Invention

This invention relates to needle protection, and more particularly, although not exclusively, relates to the protection, after use, of hypodermic syringe needles, stylettes, catheters and similar surgical or medical devices having, integrally or as an attachment, a sharp ended point for piercing or injecting and which, once used on a patient, is potentially infective. In such circumstances protection for the sharp point is highly desirable, not so much to protect the point itself from damage but to protect the user and others from the potentially infective sharp point.

It is to be understood, however, that the invention is equally applicable to any other similar sharply pointed portion of an instrument or device, such portions hereinafter being referred to for convenience as "needles".

2. Description of the Prior Art

Protection for hypodermic and similar needle ends is known in the form of caps which are fitted over all or part of the needle. However, such caps suffer from the disadvantage that it is necessary to place them in position by a movement towards the sharp end of the tip of the needle from beyond the needle. This in itself constitutes an action of risk since a mistaken or clumsy movement can lead to the needle scratching or piercing the skin of the hand or the fingers of the person trying to fit the cap. It is an object of the present invention to overcome or at least substantially reduce this difficulty and problem.

SUMMARY OF THE INVENTION

In accordance with one aspect of the present invention, there is provided a needle protector for a device incorporating a needle comprising at least one arm mounted or mountable at or generally adjacent to a hub, or blunt, end of the needle, and hinged or articulated so as to be capable of folding along the needle such as to shield and protect the tip thereof, and being positively securable in that folded disposition.

In accordance with another aspect of the invention there is provided a needle protector for a needle mounted or mountable at its hub or blunt end on a liquid holder or similar body, comprising at least one arm supported by the hub or body and articulated at or adjacent to the hub or body for pivotable movement alternatively away from and into a positively secured position alongside the needle, the or each arm having a portion adapted to cover or shield the point of the needle when the arm is secured alongside the needle.

The protective arm or arms may be part of or fitted to either the cylinder part or the plunger part of a hypodermic syringe or similar device.

The arm or arms may be supported from and attached to an annular support member which may comprise a separable attachment to the needle incorporating device. In this case the annular support may be passed over the needle from its tip until located at, or generally adjacent to, its hub end or even on the body of the device itself. Such a detachable arrangement may, for example, be shaped and adapted to fit upon a hypodermic syringe or a stylette, or a catheter or a cannula.

In an alternative arrangement, the needle protector may comprise an integral part of a needle incorporating device, and may be permanently secured thereto or formed therewith. Thus, for example, in the case of a hypodermic syringe, the arm or arms may be formed with the syringe body and may be located adjacent the hub where the needle protrudes from the body of the syringe, and may, in one embodiment having two diametrically opposed arms, when not protecting the needle, be pivotted away from the needle to lie alongside the body and constitute finger tabs for engagement by the first and second fingers respectively on either side of the syringe; operation thereof being by depression of the plunger with the thumb.

The or each needle protecting arm may be securable to the needle to locate it for protecting purposes. Thus, it may incorporate a clip engaging with the needle, or when more than one flap is used, may include a clip engaging with one or more other arms about the needle and/or with the needle itself.

In yet another alternative arrangement the protective arm or arms may be carried on a support member such as a collar (for example) mounted on the body or hub of the needle carrying device, the collar (and hence the arm or arms) being attached to the needle carrying device by means of a restraining link which may be in the form, for example, of a plastics (e.g. nylon) line or strip such that the collar can, after use of the needle carrying device, be moved outwardly from the hub or body over the needle a predetermined distance whereafter the arm or arms can be pivoted together to embrace the needle tip and then be secured thereabout. The advantage of this arrangement is that the arm or arms as such can be shorter than if the carrying collar is retained in position on the hub or body of the needle carrying device, whilst at the same time the same secure protection of the needle after use can be provided.

The or each arm may include an end flap extending transversely to the general plane of the arm so that in use it overlies the sharp point of the needle.

The arm or arms of the needle protectors may be arranged for securement about the needle in two modes. In the first mode, the securement can be of a light nature and of easy disengagement attachability, so that the needle can be protected in this manner prior to use, whilst the needle is being carried, for example. In the second mode, the securement about the needle can be relatively firm and detachable only with difficulty, so that after use, the protectors can be engaged in this mode to provide extra protection for the needle once it is in its used, potentially infective, condition. Thus, for example, where a pair of arms are used, these may be lightly mutually interengaged for the first mode of engagement, and may be tightly clipped about the needle in the second mode of securement. In an alternative, the arms can be taped together, for example, with a pull off tab, for the first mode of securement about the needle, and a secure clip provided for the second mode.

BRIEF DESCRIPTION OF THE DRAWINGS

In order that the invention may be more readily understood, embodiments thereof will now be described by way of example only with reference to the accompanying drawings in which:

FIG. 5 shows the arrangement of FIG. 1 with the protector arms in course of movement to a fully protective position;

FIG. 6 shows the arrangement of FIG. 1 with the arms in a fully closed protecting position about the needle;

FIG. 7 is an enlarged section on line VII—VII of FIG. 6; and

FIG. 8 shows an alternative attachment arrangement for the protectors.

DETAILED DESCRIPTION OF THE PREFERRED EMBODIMENTS

Figure 1:
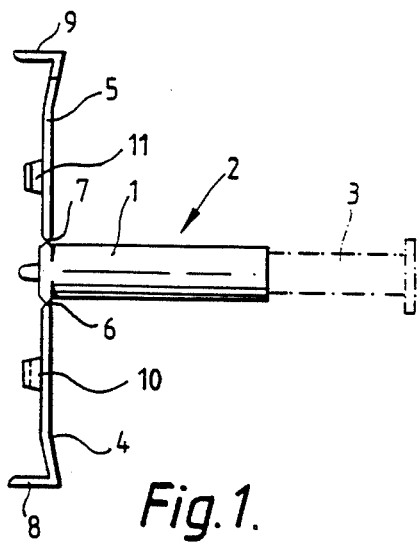
FIG. 1 is a side elevation of part of a hypodermic syringe showing the attachment of the protectors in accordance with the invention in side elevation.
Figure 2:
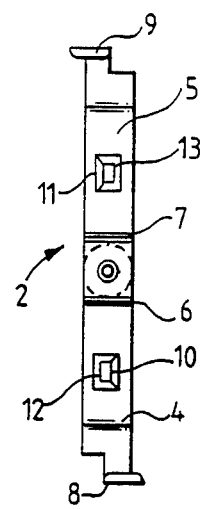
FIG. 2 shows the arrangement of FIG. 1 in end elevation.

Referring now to FIGS. 1 and 2, it is to be seen that a hypodermic syringe 2 has a cylindrical body 1 which may be formed for example of a plastics material, such as polypropylene, within which is mounted a plunger 3. the syringe has outwardly directed integrally moulded side arms 4, 5 connecting to the body 2 at its needle end via thin portions providing pivoting lines for the arms 6, 7 adjacent the syringe body. As can be seen each arm is provided at its free end with a flap 8, 9 approximately at right angles to the general plane of the arms, and additionally, part way down the arms with hook-like members 10, 11 facing forwardly of the body of the syringe adjacent generally rectangular slots 12, 13 in the arms.

Figure 3:
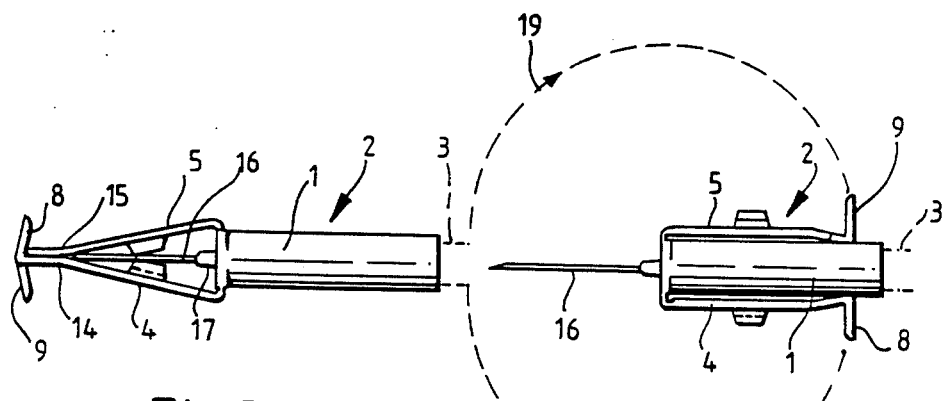
FIG. 3 shows the arrangement of FIG. 1 with the protector arms lightly engaged about a needle prior to use.

As can be appreciated from FIGS. 1 and 2 the flaps 8, 9 of the arms are capable of mutual engagement upon forward folding of the arms, and in FIG. 3 the syringe cylinder body 1, with needle 16 attached at a hub 17, is shown with the flaps 8, 9 of the two arms interengaged to protect the needle 10 of the syringe prior to use. Protection is enhanced by a slight elbow 14, 15 adjacent the needle tip, in each arm, to lay the outer portions of arms parallel to each other.

Figure 4:
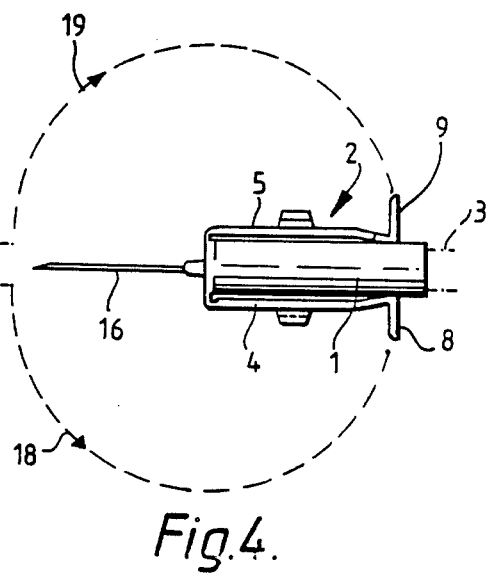
FIG. 4 shows the arrangement of FIG. 1 with the arms in a syringe using disposition.

It will be appreciated that the interengaged flaps at the ends of the arms easily disengaged from each other due to the flexibility of the plastics material concerned, and in FIG. 4 the flaps have been disengaged from their position in FIG. 3 and have been pivotted round in the direction of arrows 18, 19 so that the arms lie alongside the cylinder body of the hypodermic syringe 2, at which position the flaps 8, 9 can be used as grips for the first and second finger whilst the thumb is applied to the head of the plunger 3 for the injection of a fluid via the needle into a patient.

After use on a patient, it is highly desirable that the needle should be protected to prevent any infection or contamination thereof by the patient being transmitted by the accidental scratching or piercing of the skin of others, and for this purpose, as shown in FIG. 5 the arms may now be pivoted forward in the direction of arrows 20, 21 from behind the needle 16 by appropriate movement of the first finger 24 and thumb 25 of the operator in the direction of arrows 22, 23 to the position previously shown in FIG. 3, and then beyond this to a position of a second mode of engagement as shown in FIG. 6 where the arms are squeezed together in the directions of arrows 26, 27 adjacent the hooks 10, 11 of each, whereby the hooks 10, 11 and slots 12, 13 interengage with each other and clip over the needle 16 as is shown most clearly in the enlarged section in FIG. 7. Once the protecting arms are interengaged in this manner, they are relatively difficult to disengage so that the tip of the potentially infective needle is securely protected against the possibility of accidental scratching or piercing of the skin of anybody else and may be safely discarded into an appropriate refuse receptacle, for example.

FIG. 8 illustrates an arrangement generally closely similar to that of FIGS. 1 to 7, except that in this instance protector arms 30, 31 are mounted via thin pivot portions 32, 33, on a detachable hub 34 carrying a needle 35, the hub being mounted on a stub outlet 36 from a syringe body 37.

Pivotting of arms 30, 31 in the direction of arrows 42, 43 to lie alongside the body of the syringe 37 enables use of the syringe as in the arrangement of FIGS. 1 to 7.

Protection of the tip of the needle 35 prior to use is by means of flaps 38, 39 corresponding to those of the embodiment of FIGS. 1 to 7, and protection after use of the needle is provided by means of interengaging hooks 40, 41 again operational exactly as in the arrangement of FIGS. 1 to 7.

After use of the syringe and engagement of the hooks 40, 41, the protected needle 35 on its hub 34 can be removed from the stub outlet 36 and be discarded.

By means of the invention we have provided a safe and simple means for protecting the sharp point of a needle or similar device which otherwise would be capable of potential contamination by scratching.

It is understood that the foregoing is merely exemplary of needle protectors in accordance with the invention and that modifications can readily be made thereto without departing from the true scope of the invention.

I claim:

1. A needle protector for use with a hypodermic syringe which has a needle, a cylindrical body with a hub connecting the needle to the body and a plunger for movement within the body, the needle protector comprising a pair of arms mounted or mountable at or generally adjacent to the hub of the syringe and diametrically opposed, one to the other, on each side of the syringe, each arm being hinged or articulated so as to be capable of folding along the needle such as to shield and protect the tip thereof and being positively securable in that folded disposition, the arms additionally being pivotable away from the needle to lie alongside the body of the syringe, with the arms incorporating angled tabs or flaps constituting finger tabs for engagement by the first and second fingers respectively of a user on either side of the syringe for operation thereof by depression of the syringe plunger with the thumb of the user.

2. A needle protector as claimed in claim 1 wherein the arms are provided with clips for engaging the needle or the other arm when in the needle protective position.

* * * * *